(12) United States Patent
Harp et al.

(10) Patent No.: US 8,504,381 B2
(45) Date of Patent: *Aug. 6, 2013

(54) STRUCTURED DATA AUTHORING AND EDITING SYSTEM

(75) Inventors: Charles Edward Harp, Indianapolis, IN (US); Joe Mize, Westfield, IN (US); David C. Rhew, Los Angeles, CA (US); Victor Chiwei Lee, Los Angeles, CA (US); Bertina Monica Yen, Los Angeles, CA (US); Jeffrey Douglas Barnhart, West Hills, CA (US); Scott Weingarten, Agoura Hills, CA (US); Gregory Dorn, Manhattan Beach, CA (US)

(73) Assignee: Zynx Health Incorporated, Los Angeles, CA (US)

(*) Notice: Subject to any disclaimer, the term of this patent is extended or adjusted under 35 U.S.C. 154(b) by 1036 days.

This patent is subject to a terminal disclaimer.

(21) Appl. No.: 11/510,837

(22) Filed: Aug. 25, 2006

(65) Prior Publication Data

US 2007/0067182 A1    Mar. 22, 2007

Related U.S. Application Data

(60) Provisional application No. 60/718,169, filed on Sep. 16, 2005.

(51) Int. Cl.
*G06Q 50/00* (2012.01)
*G06Q 10/00* (2012.01)

(52) U.S. Cl.
USPC .................................................. 705/2; 705/3

(58) Field of Classification Search
USPC ............................................................ 705/2
See application file for complete search history.

(56) References Cited

U.S. PATENT DOCUMENTS

| 4,491,725 | A | | 1/1985 | Pritchard |
|---|---|---|---|---|
| 4,857,713 | A | | 8/1989 | Brown .......................... 235/375 |
| 5,664,109 | A | | 9/1997 | Johnson et al. |
| 5,786,816 | A | * | 7/1998 | Macrae et al. ................ 715/837 |
| 6,018,713 | A | | 1/2000 | Coli et al. ........................... 705/2 |
| 6,073,106 | A | * | 6/2000 | Rozen et al. ....................... 705/3 |
| 6,463,417 | B1 | * | 10/2002 | Schoenberg ..................... 705/2 |
| 6,694,334 | B2 | | 2/2004 | DuLong et al. ............. 707/104.1 |

(Continued)

FOREIGN PATENT DOCUMENTS

| WO | WO 02/19221 | 3/2002 |
|---|---|---|
| WO | WO 03/030787 | 4/2003 |
| WO | WO 2006/060572 | 6/2006 |

OTHER PUBLICATIONS

Payne, The transition to automated practitioner order entry in a teaching hospital: the VA Puget Sound experience, Proc AMIA Symp. 1999:589-593.*

(Continued)

*Primary Examiner* — Tran Nguyen
(74) *Attorney, Agent, or Firm* — Knobbe, Martens, Olson & Bear LLP

(57) ABSTRACT

The present invention offers an extensive suite of tools that facilitate and enhance the capability within a healthcare institution to establish and maintain an evidence-based best practice approach to providing patient care. Using evidence, term vocabulary and default structured content (order sets) embodiments of the invention enable the localization of said content in a well structured environment.

30 Claims, 15 Drawing Sheets

U.S. PATENT DOCUMENTS

| | | | |
|---|---|---|---|
| 7,822,626 B2* | 10/2010 | Harp et al. | 705/2 |
| 7,945,453 B2 | 5/2011 | Harp | |
| 2002/0059080 A1 | 5/2002 | Kasirer et al. | 705/2 |
| 2002/0095313 A1 | 7/2002 | Haq | 705/2 |
| 2004/0128165 A1 | 7/2004 | Block et al. | 705/2 |
| 2005/0027566 A1* | 2/2005 | Haskell | 705/2 |
| 2006/0149416 A1 | 7/2006 | Mohapatra et al. | 700/242 |

OTHER PUBLICATIONS

Fitzpatrick et al., If You Build It (Right) They Will Come: The Physician-Friendly CPOE: Not Everything Works as Planned Right Out of the Box. A Mississippi Hospital Customizes its Electronic Order Entry System for Maximum Use by Physicians (Computerized Physician Order Entry, Health Mguit. Tech., Jan. 1, 2005, 26(1).

Abstract for Goldstein, Mary K., M.D., "Ontology-Based Physician Order Sets," (1 pg.).

Abstract for Schuster et al., "Involving Users in the Implementation of an Imaging Order Entry System," Journal of the American Medical Informatics Association, 2003, (1 pg.).

Abstract for Groopman et al., "Effect of 'Standard Order' Deletion on Emergency Department Coagulation Profile Use," Annals of Emergency. Medicine, 1992, (1 pg.).

Abstract for Anderson et al., "Physician Utilization of Computers in Medical Practice: Policy Implications based on a Structural Model," Social Science and Medicine, 1986, (1 pg.).

Abstract for "Medical Test Results You Can View," Link-Up, Jul. 1, 2000, (1 pg.).

Health Management Technology's If you build it (right) they will come: the physician-friendly CPOE: not everything works as planned right out of the box. A Mississippi hospital customizes its electronic order entry system for maximum use by physicians. (computerized physician order entry) (Aug. 15, 1989).

Abstract for Overhage et al., "A Randomized Trial of 'Corollary Orders' to Prevent Errors of Omission," J. Am. Med. Inform. Assoc., 1997, vol. 4, No. 5, (1 pg.).

Franklin et al., "Modifiable Templates Facilitate Customization of Physician Order Entry," Proc. AMIA Symp., 1998, pp. 315-319, (6 pgs.).

Pallato, John, "Health-Care Software Takes Care of Records, Helps Staff Plan Ahead," PC Week, Jul. 7, 1987, vol. 4, No. 27, p. 117 (1 pg.).

Samet et al., "Development and Implementation of a Multidisciplinary Review and Approval Process for Pre-Printed Physician Orders," ASHP Midyear Clinical Meeting, 2005, vol. 40, (2 pgs.).

Tjahjono et al., "Promoting the Online Use of Radiology Appropriateness Criteria," Radiographics, 1999, vol. 19, No. 6, pp. 1673-1681, (9 pgs.).

* cited by examiner

STRUCTURED DATA AUTHORING AND EDITING SYSTEM

RELATED APPLICATIONS

This application claims the benefit of U.S. Provisional Patent Application Ser. No. 60/718,169, filed on Sep. 16, 2005, entitled "Structured Data Authoring and Editing System," incorporated herein by reference.

BACKGROUND

Proprietary tools exist to allow healthcare order set content to be customized within the context of a vendor's particular data authoring and customizing system. However, such single-vendor systems may be overly constraining where an organization needs to customize content for use with systems and applications from multiple vendors. One exemplary approach to address this issue might be for industry participants to establish an industry-standard format or toolset for order set content authoring and customization. However, to date, an industry standard has not arisen and toolsets for review, customization and integration of evidence based content structures are generally sponsored by a single healthcare application vendor and designed to best fit with that vendor's environment. Advantages may be obtained by a toolset that allows for the improved sharing of data between multiple vendor health care data management systems.

SUMMARY OF THE INVENTION

The invention relates to a system and methods for the review, customization and integration of health care-related content structures, also referred to as clinical content. In various embodiments, a platform for the review, customization and integration of such content structures and, in one exemplary embodiment, for the review, customization and integration of order sets, used in healthcare applications is disclosed. One such example implementation of such an embodiment is referred to as the "Zynx" platform and the authoring environment of that platform is referred to as "AuthorSpace." It should be understood that the Zynx platform is presented as an exemplary non-limiting implementation, and that features of the platform and authoring environment may or may not be included in a particular implementation or embodiment.

Some embodiments may help users take steps to reduce undesirable variations in patient care and help such users make decisions intended to facilitate improvements in quality, safety, and efficiency of patient care. In general, some embodiments may help inform clinicians at the "point of care" about evidence-based or scientific approaches to diagnosing and treating patients that could, in turn, help those users to achieve the best possible patient outcomes. In some embodiments, this information is provided in a manner that can be integrated with existing health care information technology, including computerized physician order entry and electronic health records, including, for example, billing information, or other patient or clinical information.

In one embodiment, a service provider, also referred to as an information provider, may create electronic content, such as order sets. An example of such a service provider is Zynx Health Incorporated, of Los Angeles, Calif. Order sets may represent a collection of orders and notations that are relevant to treating a given condition under a given set of circumstances based upon current evidence. The order sets created by a service provider may be a superset of order items available at a healthcare institution (and, in a typical implementation, will contain all relevant order items). Since most healthcare institutions do not have an all-encompassing selection of treatments and services, the order set content must be tailored by an institution to the items that such institution is prepared to provide. This process of tailoring may be referred to as customizing the order set.

In some embodiments, an environment may be provided that allows the providers of care, for example a single practitioner or practitioner group, clinic, hospital, urgent care facility, nursing home, health network, or some combination, to customize and share clinical content. It may even be shared across multiple potential healthcare systems. To do this, some embodiments provide a tool that allows for the creation of content using a common nomenclature and structure, to facilitate the customization of the content to fit the needs of the healthcare institutions via a intuitive user interface and, upon completion of the customization process, transforms the content dynamically into a format that could be consumed by the healthcare application(s) used by the institution.

Some implementations may also provide added value to the authors/editors customizing the content by allowing them to use an authoring environment for editing clinical content provided by others in addition to initial creation of content. To do this, some embodiments provide tools to maintain integrated content beyond the order set, to maintain the integrity of the content, and to preserve each version of the content over time for the purposes of historical reference.

Some implementations may also take into consideration certain local preferences and have the ability to be aware of local workflow. Some implementations may also provide content management environments that support the consumption of the content by other systems. This, for example, allows health networks to exchange relevant data with multiple applications across an institution as well as at separate institutions with different healthcare applications.

Some embodiments may be designed to solve a number of problems with existing order set management applications, and bridge the integrated content gap between healthcare applications. In some embodiments, a web-based software application is designed to allow customers of an information provider (e.g., an evidence-based information provider) to create and customize evidence-based structured content for the purpose of users' integration into the healthcare system of their choice. Other embodiments, e.g., in stand-alone applications, may also be used.

Structured content such as that created in an authoring environment may be based on a predefined vocabulary of terms, referred to as a PIVOT catalog (Portable Intermediate Vocabulary of Objective Terms). The created content may be any sort of health care or related content, including without limitation order sets, plans of care, rules (e.g., rules for alerting), alerts, protocols, performance measures, and/or structured documentation. The created content may include combinations of these, and may also include other information, such as links to relevant evidence documentation or practice patterns. In some embodiments, when an end-user wants to use the structured content created in an authoring environment in their healthcare application, they can use an export functionality to convert the content into pre-coordinated terms that will work in their target application. The export format itself may be customized to each target system for ease of import. The combination of the standard content format and the custom exports and vocabulary transformation allows content authored in such an authoring environment to be portable. Content authored by one user, if shared, could be used by another user regardless of their healthcare system vendor or local terminology.

In some embodiments, an authoring environment is provided that is a virtual place where like users can work together on authoring content. Administrators can create teams within an environment as well as define local milestones and review content created/edited by others. A typical scenario is a single environment supporting the users for a given institution, such as a hospital or nursing home. In some cases, an environment can represent one practitioner group office, or an entire health network that includes several hospitals. Typical implementations of such an environment may support user-based security features. For example, in a typical implementation, access to the authoring environment requires a username and password. Users are given certain privileges with respect to content in their environment by the environment administrator, which is typically a power-user from the hospital or health network. In addition, audit features may be implemented so that changes made to content in an authoring environment can be tracked and audited.

In general, in one aspect of the invention, a method for review and adoption of an evidenced-based content structure includes selecting an evidenced-based content structure. The content structure may be provided, for example, by an information provider, a user, a related institution, or by another person or entity. The content structure may be any sort of content structure, but in one preferred embodiment is an evidence-based order set. The method also includes duplicating the structure in an authoring environment and reviewing the duplicated structure. The method also includes customizing the structure based on the review, releasing the customized structure and integrating the structure into an application environment. In some embodiments, the evidenced-based content structure may include an order set.

In various embodiments, one, two, or three of these steps may be included or omitted, for example, the step of duplicating the structure may be optional, the step of integrating the structure into an application environment may be optional, and/or the step of customizing the structure in response to the review may be optional.

In some embodiments, the content structure may be integrated into multiple application environments, which may be, for example, the same or different types of application environments. Moreover, in various embodiments, the application environment may be a healthcare environment, a healthcare information technology (HIT) application environment, a live HIT application environment or another suitable environment. In various embodiments, the method may be implemented by a web-based system, for example, such that users may use a web browser to access the system. The system can check username and password, and assign privileges to each user. The duplicated structure may be reviewed in a variety of ways, for example by an internal review, a public review, or by comparing the structure against local practice and/or a catalog. The method also may include exporting the structure in a vendor format or vocabulary, or translating the structure.

In general, in another aspect of the invention, a system for review and adoption of an evidenced-based content structure comprises a content library for selection of a content structure. The system also includes a content manager for duplication and eventual release of the content structure and a content review tool for review of the structure. The system also includes a content editor for customization of the structure, and an environment manager for integration of the structure into an application environment.

In general, in another aspect of the invention, an article of manufacture having computer-readable program portions for review and adoption of an evidenced-based content structure comprises computer-readable instructions for selecting an evidenced-based content structure, duplicating the structure, reviewing the duplicated structure, customizing the structure in response to the review, releasing the customized structure, and integrating the structure into an application environment. As described above, in some embodiments, the structure is integrated across multiple environments, and in other embodiments the computer-readable instructions may implement a web-based system.

In general, in another aspect, a method for updating a revised evidenced-based content structure includes drafting a first structure provided by a user, reviewing the first structure, releasing the first structure, drafting a second structure, reviewing the second structure, releasing the second structure, and retiring the first released structure. The evidenced-based content structure preferably may be an order set. In some embodiments, the method is performed by a web-based system. The reviewing step may be performed, for example, by an internal review, a public review, by comparing the structure against local practice and catalog, or some combination. In some embodiments, drafting a structure may include editing the structure. In other embodiments, reviewing a structure disables editing capabilities. Moreover, releasing a structure may include stamping the structure with a version number or may permanently lock the structure. The method may further include permanently storing retired structures.

In general, in another aspect, a system for updating a revised evidenced-based content structure comprises a content manager for drafting of a first structure provided by a user, review of the first structure, release of the first structure, drafting of a second structure, review of the second structure, release of the second structure, and retirement of the first released structure. The system can also include permanent storage of retired structures.

In general, in another aspect, the invention relates to an article of manufacture having computer-readable program portions for updating a revised evidenced-based content structure comprises computer-readable instructions for drafting a first evidenced-based content structure provided by a user, review of the first structure, release of the first structure, drafting of a second structure, review of the second structure, release of the second structure, and the retirement of the first released structure.

In general, in another aspect, the invention relates to a system for review and export of an evidenced-based content structure. The system includes an authoring environment for reviewing and/or editing the structure. The system also includes a vocabulary transformation engine for transforming the structure into a standard structure as well as a custom export engine for converting the standard structure into an export structure in a particular vendor system format. In various embodiments the evidenced-based content structure may be an order set. In some embodiments the system is web-based. The authoring environment may include a content library, a content editor, a content manager, a content review tool, a global content editor, a notification manager and an environment manager. The system may include multiple custom export engines, each for converting the standard structure into respective export structures in different vendor system formats.

In general, in another aspect, a method for automated conversion of an evidenced-based content structure includes selecting a structure provided by a user, transforming the structure into a standard structure, and converting, through an automated process, the standard structure into an export structure in a particular vendor system format. In some embodiments the method may be implemented by a web-based system. The evidenced-based content structure may be an order set. In other embodiments, the standard term vocabulary may be mapped to multiple target vocabularies. The target vocabulary may be a national standard code (e.g. SNOMED, LOINC, NDC's, CPT4, ICD9-CM, and so on), a vendor vocabulary, or a local catalog vocabulary.

In general, in another aspect, a system for mapping an evidenced-based content structure to a target vocabulary uses a vocabulary map which transforms the structure into a standard term vocabulary and maps the standard term vocabulary to a target vocabulary.

In general, in another aspect, a system for collaborative review of an evidenced-based content structure includes first and second authoring environments for reviewing and/or editing the structure. In the system, users in each authoring environment are granted access only to their authoring environment (i.e., a user in the first authoring environment is only granted access to the first authoring environment, and a user in the second authoring environment is only granted access to the second authoring environment). In some embodiments, the authoring environments are each associated with hospitals. In some embodiments, if the authoring environments are related through a common network (i.e., a common health network) a user in the first authoring environment may be granted some degree of access to the second authoring environment and in other embodiments, a user in the second authoring environment may be granted limited access to the first authoring environment. In some embodiments, a user's access to an authoring environment is controlled by a password, or their access is granted based on their role on a team. A user's access may be view-only or may include content rights.

In general, in another aspect, a method for collaborative review of an evidenced-based content structure (i.e., an order set) which includes providing a first and second authoring environment for reviewing and/or editing the structure, and granting access to a user in the first authoring environment to the first authoring environment only and granting access to a user in the second authoring environment to the second authoring environment only. If the authoring environments (which can be associated with hospitals, or other medical offices, practices institutions, or facilities and so on) are related through a common network such as a common health network, a user in the first authoring environment may be granted limited access to the second authoring environment. A user's access to an authoring environment may be, for example, view-only, or may include content editing permissions.

In general, in another aspect, a method for managing a life cycle of an evidenced-based content structure includes adding and updating specific lifecycle events to the structure, posting a review of the structure, viewing the review of the structure, displaying a change in the structure, marking the structure as a protocol, and publishing the structure for use within an environment's view space. In various embodiments the environment is a healthcare environment. The changes made to the structure may be logged in an audit trail database and when marking the structure as a protocol, the structure may be virtually linked into another structure. Moreover, when publishing the structure into an environment's viewspace, non-authoring environment users may see the structure in a non-authoring environment website.

In general, in another aspect, a system for managing a life cycle of an evidenced-based content structure (i.e., an order set) includes a content manager with a module for adding and updating environment specific lifecycle events to the evidenced-based content structure. The system also includes a module for posting a review of the structure and a module for viewing the review of the structure. The system also may include a module for displaying a change in the structure, a module for marking the structure as a protocol, and a module for publishing the structure into a view space.

The details of one or more embodiments of the invention are set forth in the accompanying drawings and the description below. Other features, objects, and advantages of the invention will be apparent from the description and drawings, and from the claims.

DETAILED DESCRIPTION OF THE INVENTION

The present invention offers a unique approach to the selection and localization of clinical structured content (e.g., evidence-based structured content) in order to facilitate the rapid development and regular update of these structures. An implementation will be described with reference to FIGS. 1-15.

Figure 1:
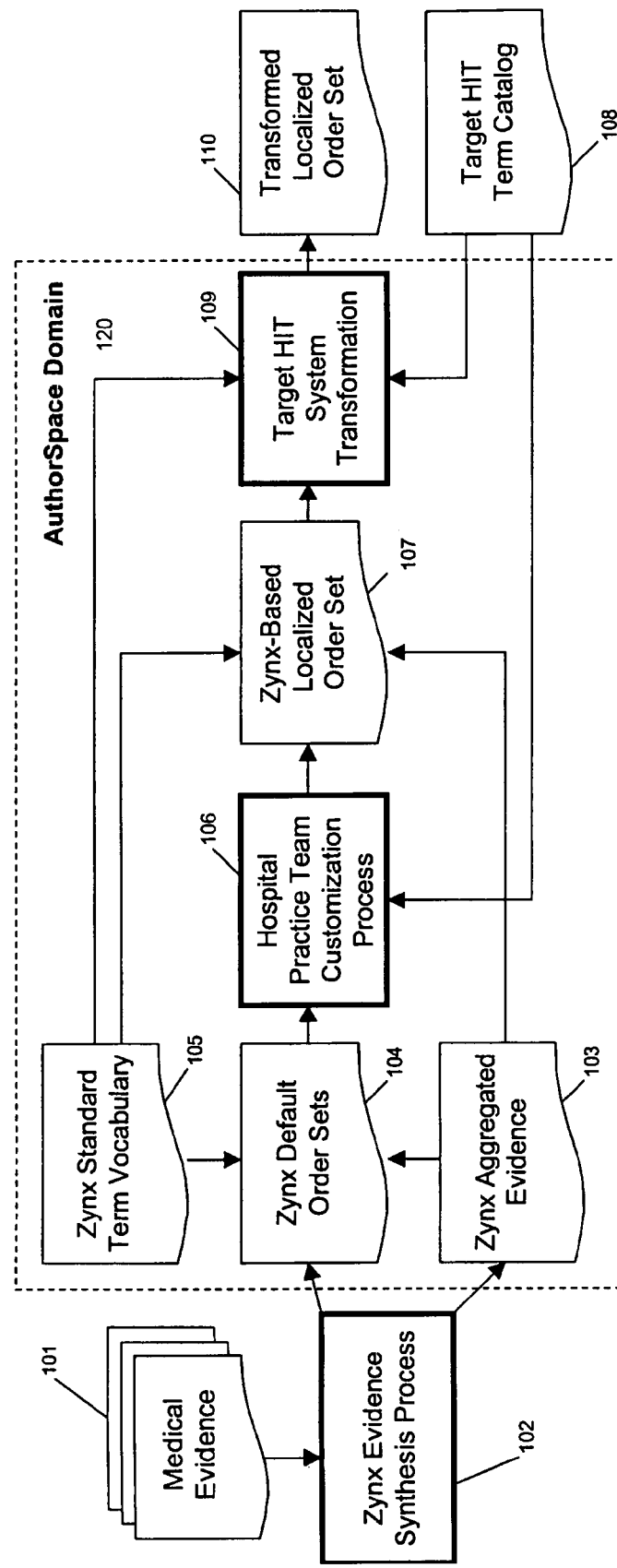
FIG. 1 is a schematic illustration of the process flow of the system of the present invention.

Referring to FIG. 1, embodiments of the present invention may facilitate the rapid development of clinical content structures, such as evidence-based order sets, for use in the practice of delivering patient care. Generally speaking, an information provider, which may be an organization, team, third-party supplier, and so on, monitors the state of the evidence for selected clinical situations and produces evidence overviews that suggest certain practices. This typically includes review of medical journal articles and publications, but also may include reviewing unpublished studies, internal reviews and data aggregation, and the like. In some embodiments, there may be one, two, or more information providers.

This evidence-based content is used by the information provider to construct a superset of order sets that are suggested by the evidence. These order sets are useful in their own right, and to provide further advantages in the use of such evidence and order sets (and/or in use of other types of data), embodiments of the present invention provide an environment for the end user (typically one or more medical practitioners) to review the suggested orders in a collaborative setting and make changes to reflect the local availability of order items and common practice, and to then quickly integrate the localized content into healthcare application from various vendors.

As shown in the figure, in one embodiment, medical evidence 101 is used in an evidence synthesis process 102 to generate aggregated evidence 103 as well as default order sets 104. The synthesis 102 may include comparing or reviewing evidence that was considered in the past, as well as new evidence, to form a synthesis of available evidence. The default order sets are order sets that are generated as a result of the synthesis 102 of the evidence 101. The default order sets 104 may be in a standard term vocabulary 105 as described further herein.

The default order sets 104 are provided in an authoring environment, shown in the diagram as the AuthorSpace authoring environment 120. The authoring environment 120 allows a practice team 106, such as a hospital practice team to review and customize the default order sets 104. This may involve extensive review by a number of people, by all relevant practitioners within a facility, or by a selected group or committee of practitioners. The result of the customization process 106 is a localized order set, stored and maintained within the authoring environment 120. The localized order set 107 may be unchanged from the default order set 104 or may be modified as a result of review and modification during the customization process 106. Following completion of the review, the localized order set may be transformed 109 into a format suitable for a "target" health information technology (HIT) system that is used by the practitioners in question. For example, the target HIT system may be the HIT system for a hospital, medical facility, or doctor's office The transformation 109 makes use of the standard term vocabulary 105 used in creating and storing the default order sets 104 as well as information about the target HIT system 108. This information may include a target HIT term catalog, which is information about the terms used or expected by the target HIT system. The localized order set 107 is transformed 109 into the transformed, localized order set 110, preferably into a format that will allow the transformed, localized order set 110 to be imported easily into the target HIT system.

It should be understood that the techniques described with respect to FIG. 1 are applicable to any sort of clinical content, including without limitation order sets, plans of care, rules (e.g., rules for alerting), alerts, protocols, performance measures, and/or structured documentation. Here, order sets may represent a collection of orders and notations that are relevant to treating a given condition under a given set of circumstances based upon current evidence. Plans of care refers to plans developed with health professionals that identify treatment needs, goals, and objectives of a participant based on clinical assessments, and may provide strategies for meeting goals and objectives and evaluating participant's progress. Rules and alerts refers to guidelines that show how evidence may be translated into alerts and/or reminders within electronic medical record systems. Performance measures refers to a process or outcome that addresses healthcare quality and safety. Structured documentation refers to documentation of a patient's physical structure as may be included in medical records. The authored content may include combinations of these, and may also include other information, such as institutional data, policies, medical records, and meta data, which may include links to relevant documentation (e.g., evidence or practice patterns).

Figure 2:
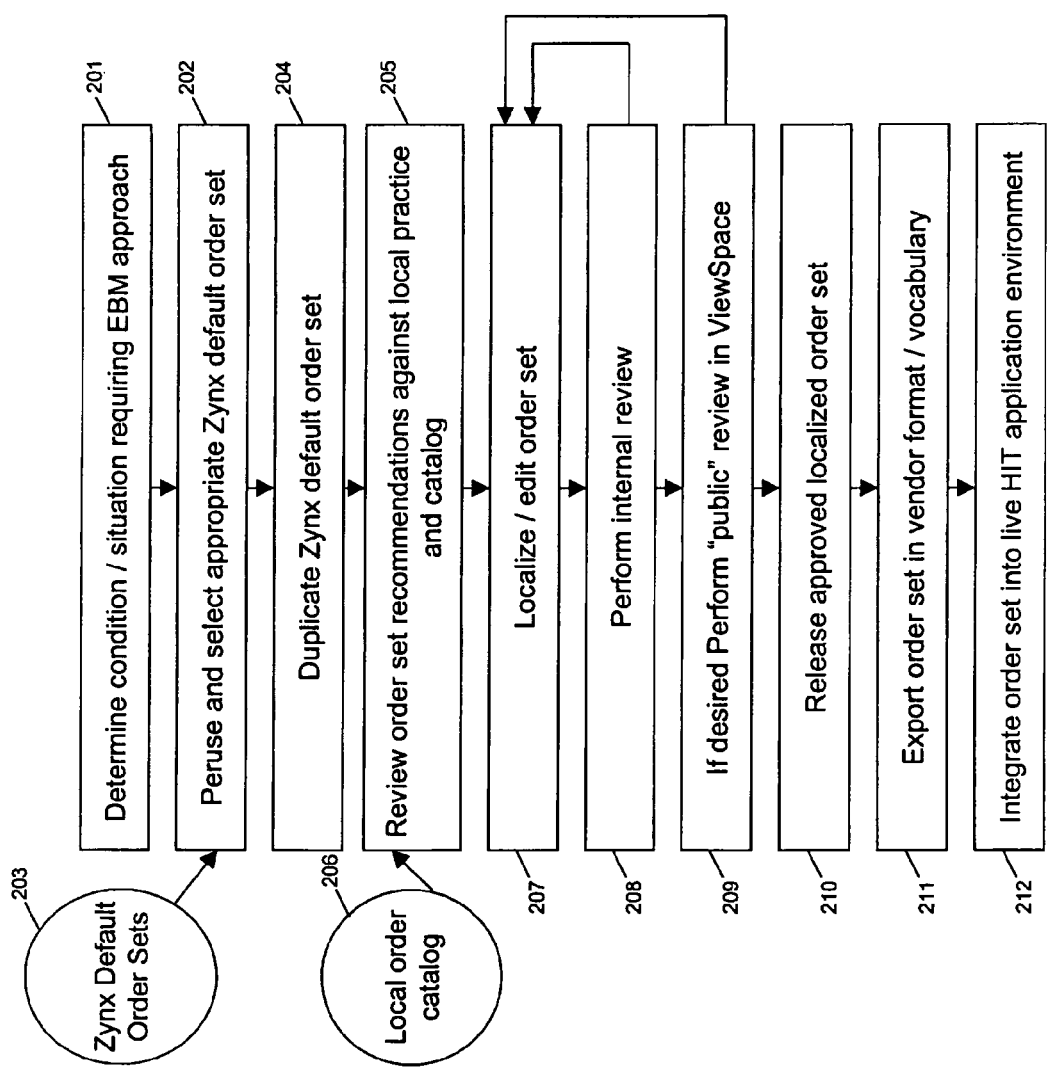
FIG. 2 is a schematic illustration of the end user workflow supported by the system of the present invention.

Referring to FIG. 2, a method for use of an authoring environment, for example by a user is shown. In one embodiment, a medical practitioner, group of practitioners, and/or institution may begin by determining the medical condition or situation that requires clinical content, such as an evidence-based order set 201. This could be, for example, based on their current outcome information or based on information from a provider, for example the EVIDENCE-BASED FORCASTER, available from Zynx Health Incorporated of Los Angeles, Calif. After identifying the relevant health condition(s), the user may perform content navigation in the authoring environment to peruse and select the default content 202 available in their order set database 203. The default order sets may be order sets from an information provider 203 or they may be from another suitable source, such as a related facility, or otherwise. They duplicate the default order set 204, for example, copying it into one of the folders in their authoring environment. One or more users then may review the recommended orders against their local order catalog 205 and against local common practice patterns either individually or in a collaborative work session. (it should be understood that many other usage scenarios are possible). The user(s) can then edit the order set 207, for example to localize it, perform an internal review 208, and if desired, allow for a public or more general review 209. The localized order set then may be approved and released 210. The order set is exported 211 into the specific vendor format and vocabulary for the HIT application environment. The order set is then integrated 212 into the live HIT application environment.

Again, it should be understood, that while the example of FIG. 2 is described with respect to order sets, embodiments of the invention may be applicable to any content that is agreed upon by a group and adopted and integrated into an information technology system. The system has particular applicability for use with clinical content, because such content typically is commented and agreed on by groups of practitioners within an office, institution (e.g., hospital, clinic, urgent care center, nursing home, group practice, emergency department, etc.), health care network, and so on prior to adoption, and also may be useful in other types of environments that have similar needs, even outside of health care.

Figure 3:
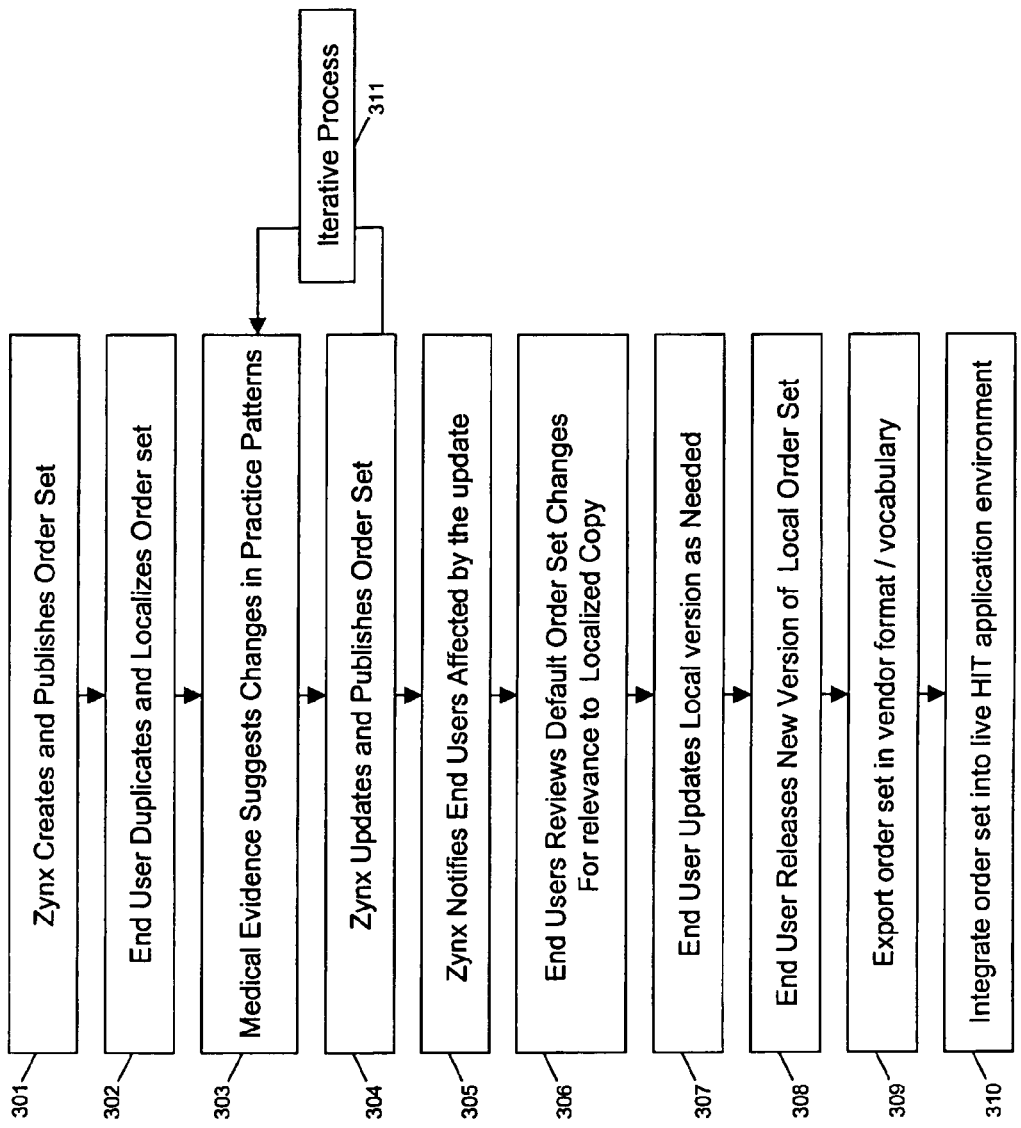
FIG. 3 is a schematic illustration of the nature and process flow related to the update process supported by the system of the current invention.

Referring to FIG. 3, in some implementations, the system can also include features to ensure that content remains up to date as time passes and new relevant information becomes available. How the changes in the evidence and practice affect the life cycle of an order set in one embodiment is depicted in the figure. Initially, an information provider creates a new order set based on the evidence for a given situation 301. The user then chooses to duplicate and localize same and releases it for use in their institution 302. The medical evidence can change over time 303 and when that occurs, the information provider may update the order set and publish it into authoring environment 304, for example as a new version of the order set. Publishing the new version of the order set will trigger a notification to those users that duplicated the previous version 305 so that they can review the differences 306, update their local version as needed 307, release 308, export 309 and integrate the new version into their healthcare application 310. This process may be iterative 311 as the evidence changes over time.

Figure 4:
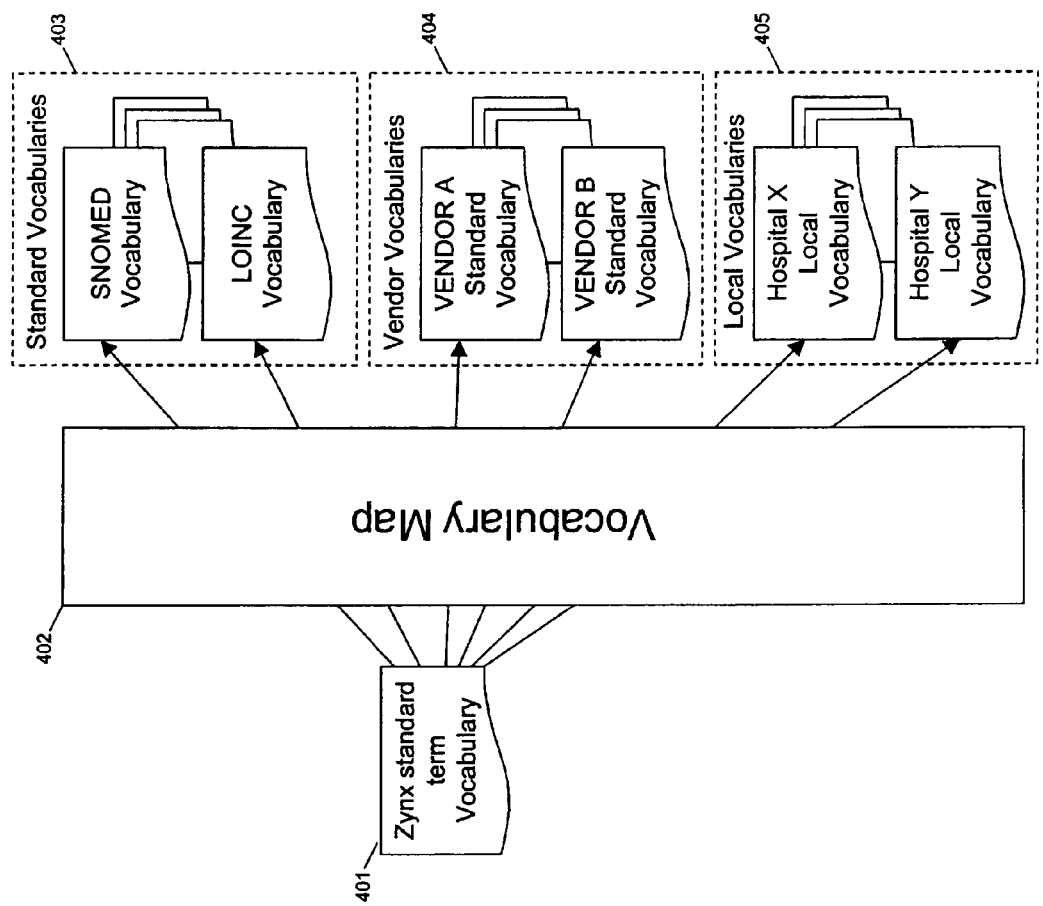
FIG. 4 is a schematic illustration of the mapping process that facilitates essential transformation of terminology in the system of the present invention.

Referring to FIG. 4, depending on the HIT healthcare application, the target vocabulary of the final version of the file could be a standard vocabulary 403 (which may be a national standard code, such as SNOMED, LOINC, NDC's, CPT4, ICD9-CM, and so on), a vendor vocabulary that spans vendor customers 404, or a local catalog just for (or specific to) the location (e.g., hospital, clinic, urgent care center, nursing home, group practice, emergency department, healthcare network, or other facility) in question 405. A vocabulary mapping functionality 402 allows for the mapping of any of these to a standard term vocabulary 401, which is used for storing and maintaining the order sets while they are in the authoring environment, and before they are transformed into the local format 403, 404, 405.

Figure 5:
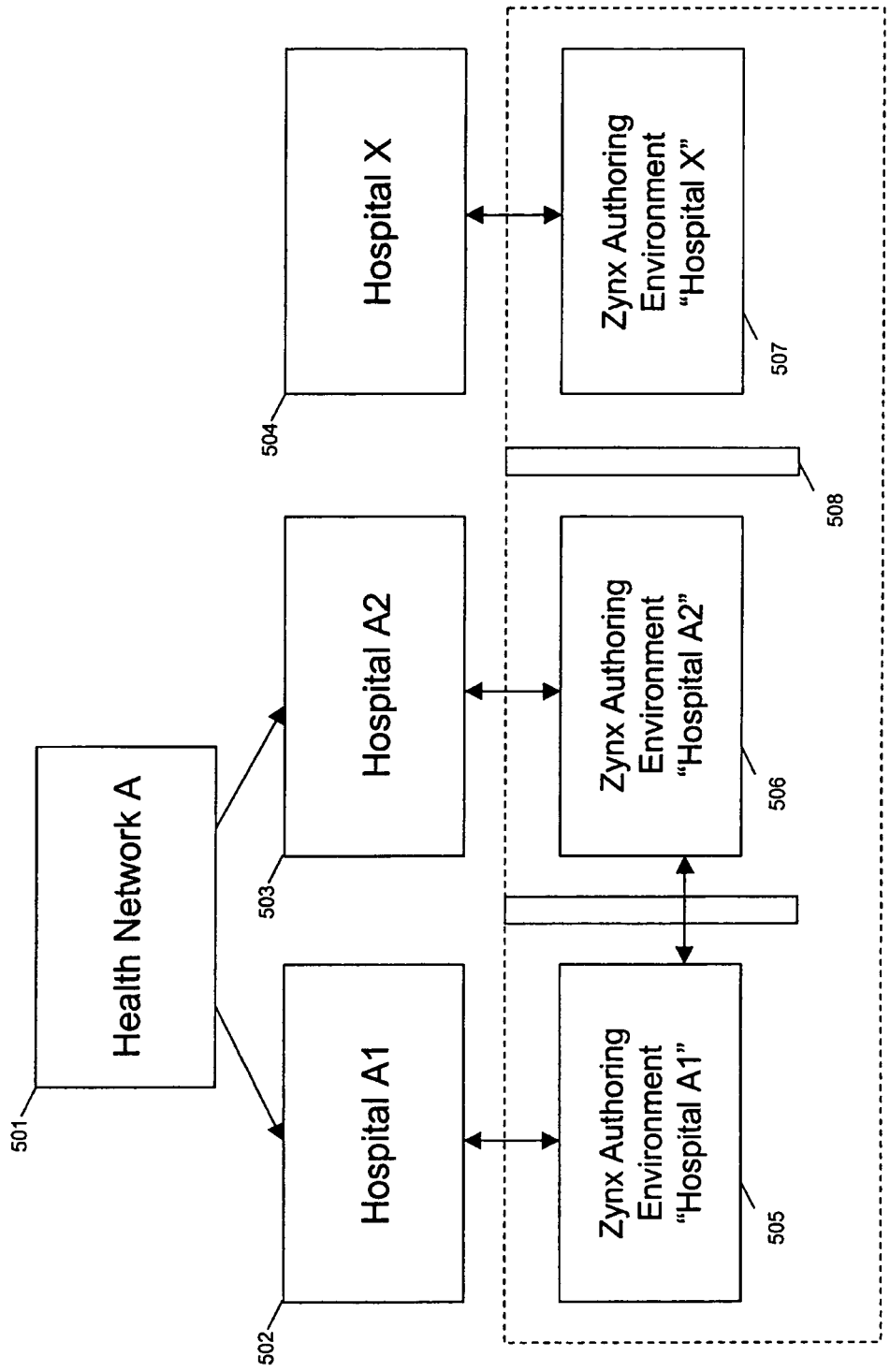
FIG. 5 is a schematic representation of how healthcare institutions are allocated authoring environments in the system of the present invention.

Referring now to FIG. 5, separate working environments for each facility (e.g., hospital, clinic, urgent care center, nursing home, group practice, emergency department, etc.) may be supported. Thus, an exemplary hospital, shown as HOSPITAL X, 504 can have a dedicated environment 507. Within such an environment (e.g., 507) users have access to the content they have localized and can define their own milestones and environmental preferences. The content and preferences defined in one environment, e.g., 507, may not be accessible to users in other environments (e.g., 505-506) as the authoring space may segregate content virtually 508 through its data structures. However, in some cases (e.g., when several hospitals are related through a common health network 501, 502, 503), access to environments of other users or institutions may be desirable. This can be provided through a mechanism in an authoring environment for the creation of related environments. Where related environments 505, 506 have been established, the environments of related hospitals 502,503 can be viewed by each other. If so configured, the related environments may allowed editing and commenting by users associated with a related environment, without the risk of content corruption.

Figure 6:
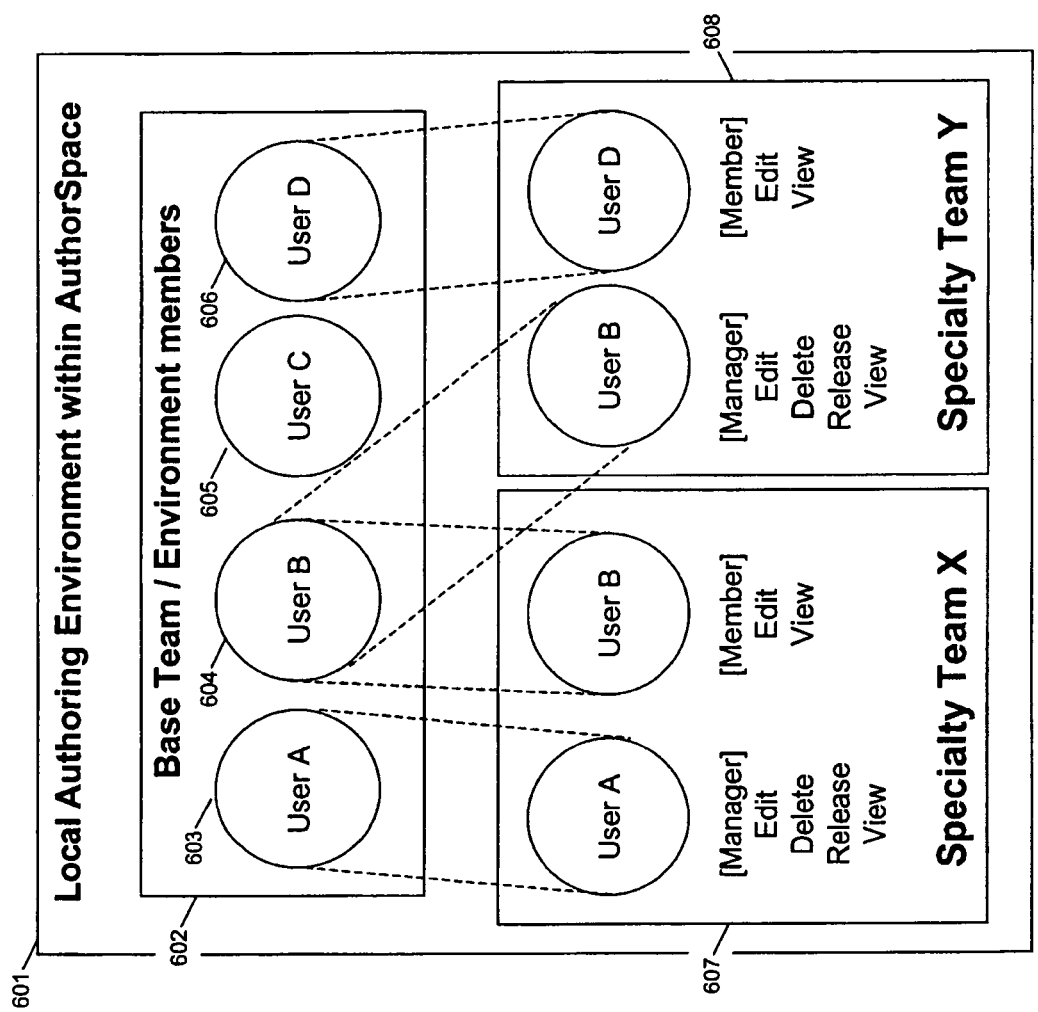
FIG. 6 is a schematic representation of how users are allocated to authoring teams within environments and assigned privileges to perform certain functions in the system of the present invention.

Referring to FIG. 6, in a typical implementation, access to an environment is protected by unique logins and passwords, with associated access privileges. A user accessing an authoring environment typically may access content only in the manner that has been defined in their access profile. The figure shows four exemplary users, USER A 603, USER B 604, USER C 605, and USER D 606. All users 603, 604, 605, 606 within an authoring environment 601 are members of what is called the base team 602. Base team membership allows the users "view-only" access to the full set of content in the environment. Within an environment the end user can establish teams (e.g., SPECIALTY TEAM X 607, SPECIALTY TEAM Y 608) for the creation of content and within those teams the users may be granted rights based upon their role on that team. Some users 605 may not be assigned to a content team but may just be allowed view rights in the authoring environment.

Figure 7:
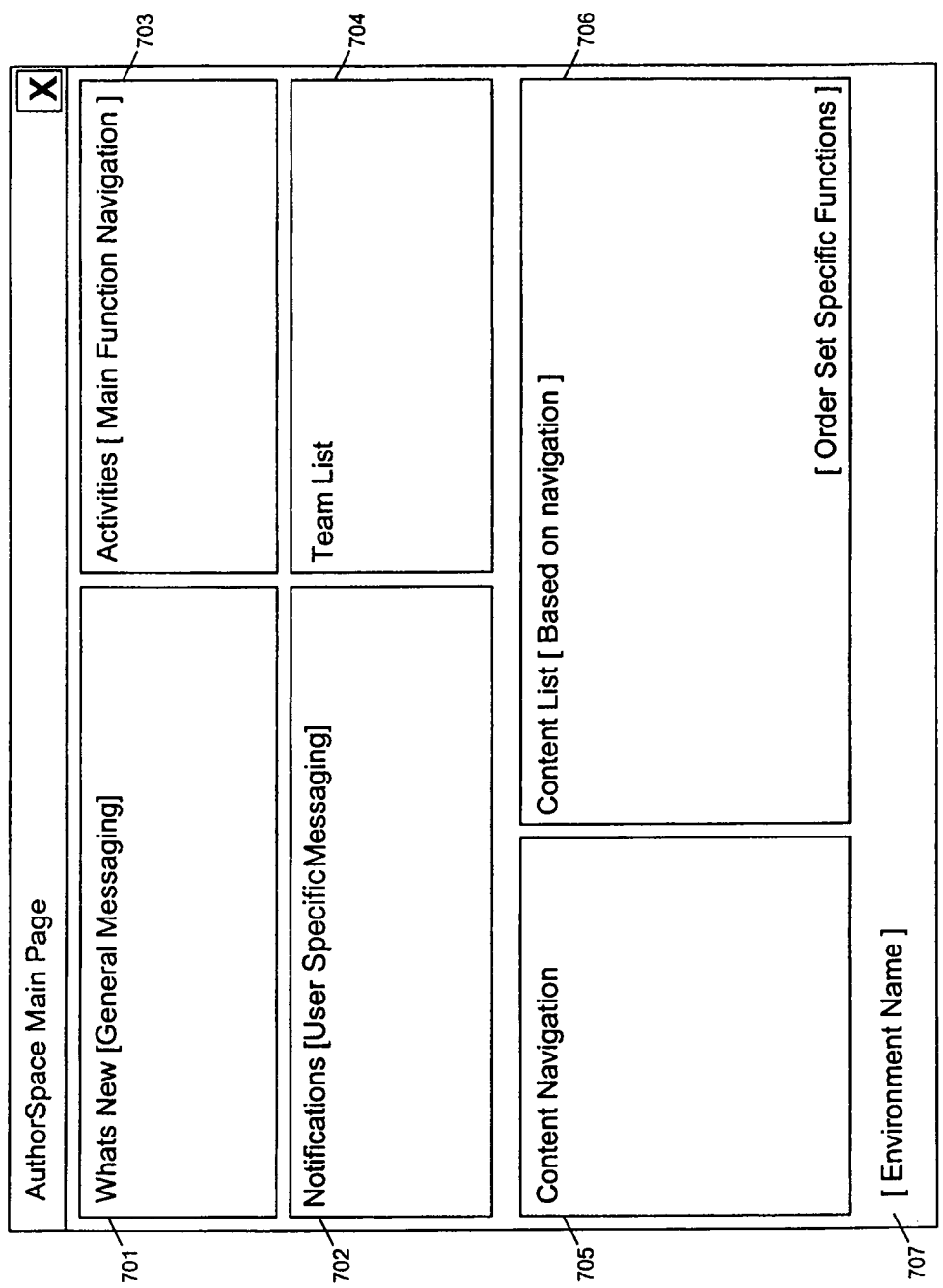
FIG. 7 is an illustrative example of the user interface in a preferred embodiment of the present invention displaying the main information, search and navigation page.

Referring to FIG. 7, once a user has accessed an embodiment of an authoring environment, the initial page encountered by the user may be the main page as depicted in the figure. On this page, a user can view general announcements or messages 701, see individualized notifications regarding their environment or content 702, see a list of the teams they are currently on 704, access additional functionality they may have access to 703 or peruse content for editing or management 705,706. Since some users can access multiple environments the environment may be displayed on this page as well 707.

Authoring and Managing Content. Beyond environment administration there are two major functions with regard to content development in an embodiment of an authoring environment: the content library, editor, manager, review tool and global content editor.

The content library is where the user can search for content to edit, customize or manage. This library may be located in the main screen as depicted in FIG. 7. This library is organized into primary folders based on the source of the content and then into sub-folders that have been categorized by the aforementioned content source. In every case there are at least two source folders, one for default content, for example as provided by a service provider, and one for the environment's local content. If the user has rights to see other content sources (e.g., from communities, vendors, etc. . . . ) they would see source folders for them as well. The user can navigate the folders or can execute a search across the folders for specific content meta data. (e.g., reason, venue, author, status . . . ). Once selected, a user can edit, manage, delete, duplicate, print or export a content item.

Figure 8:
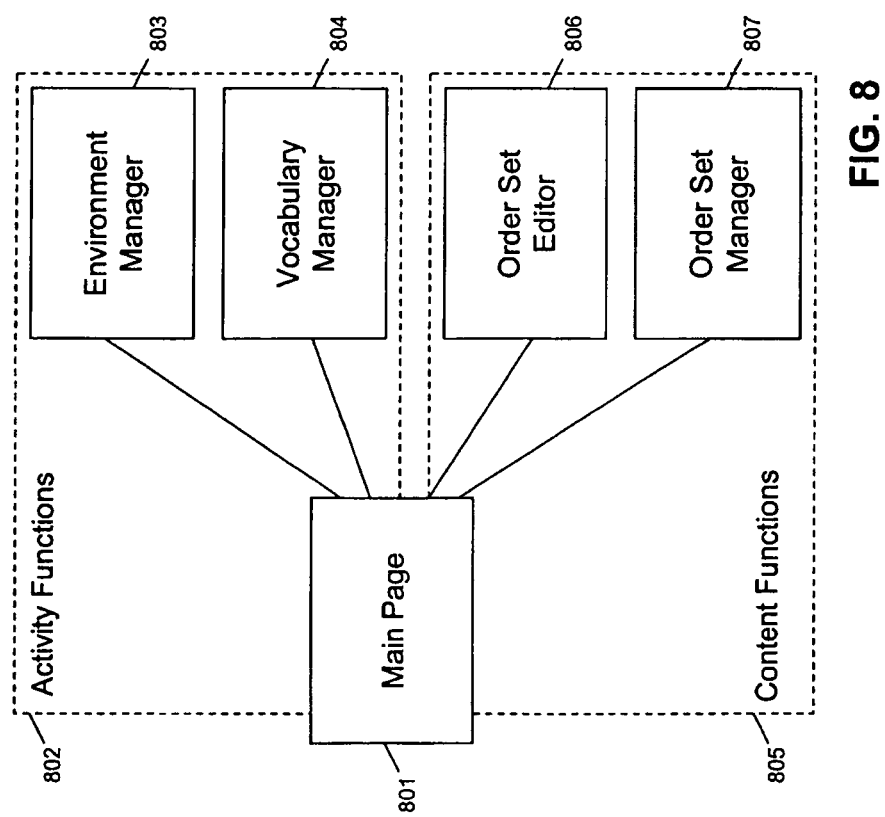
FIG. 8 is a schematic representation of the functions accessible from the main information, search and navigation page of the system of the present invention.

Referring to FIG. 8, general navigation from the main page is depicted in this exemplary embodiment. From the main page 801, the user can perform content functions 805 or other activity functions 802. Activity functions may include environment management 803 which allows certain users to modify the preferences, milestones and storage organization of the environment and vocabulary management 804, which allows the user to import local order catalogs and map them to standard terms. Content functions include viewing content, editing content 806 and managing content 807.

Figure 9:
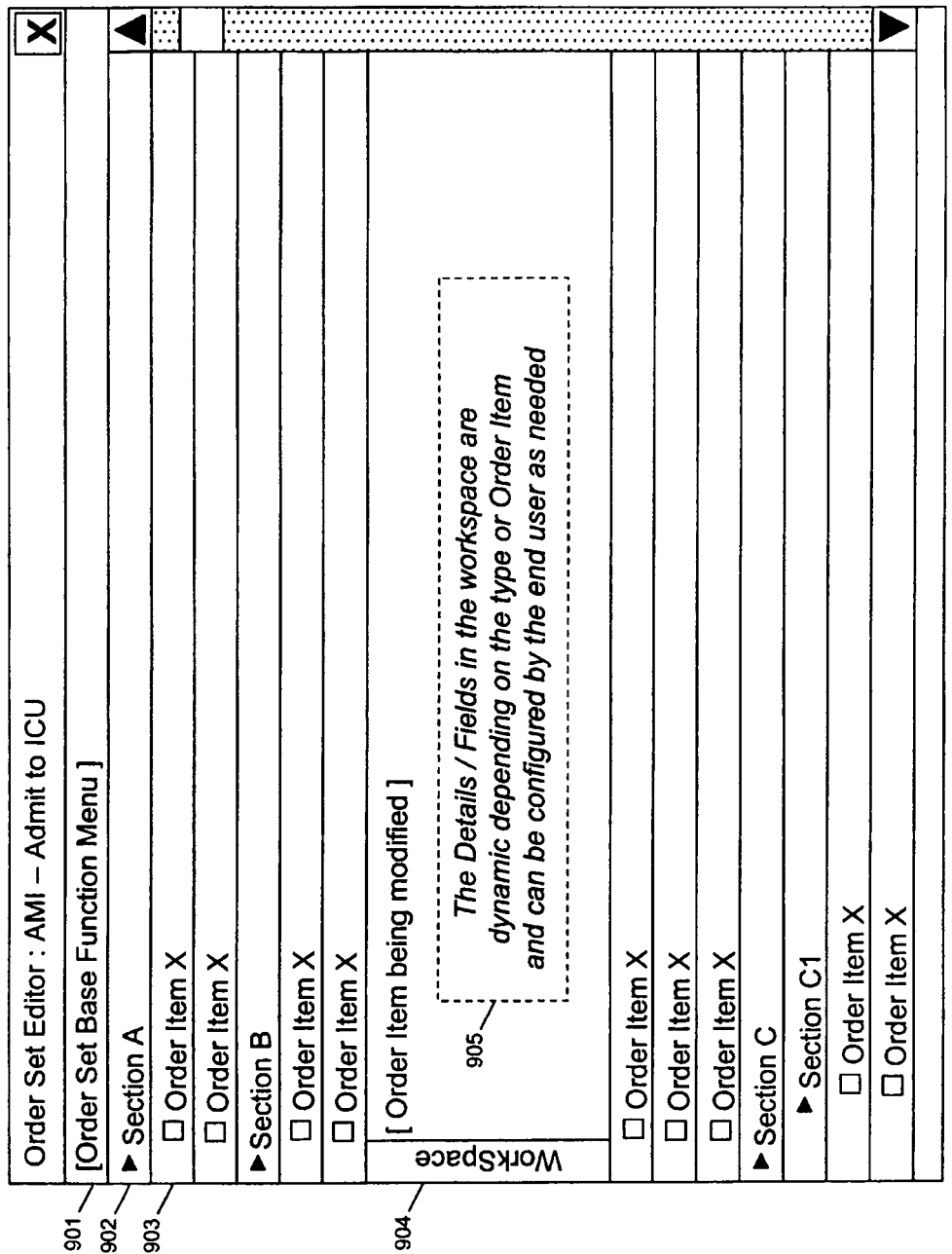
FIG. 9 is an illustrative example of the user interface in a preferred embodiment of the present invention displaying the order set editor.

Referring to FIG. 9, the content editor is an application that allows the user to modify structured content. An exemplary embodiment of an order set content editor is depicted in the figure. This interface is designed to accommodate organizing healthcare activities, orders and reminders into a logical structure dictated by the content author. Thus, the localization of the order set occurs in the order set editor.

The editor displays the order set in a hierarchical structure with sections 902 and order items 903. At the top of the editor is a collection of base functions that can be performed on the order set. These items are dynamic and can change depending on the order set in the editor. They include adding sections to the root level of the order set, removing flagged items, inserting external order sets, un-deleting removed items, and closing or checking the order set back in. While editing the order set, the user can select an item 902, 903 in the order set structure and open a workspace 904 to edit the item. The user interface within the workspace is dynamic and changes depending on the nature of the item being edited. An example might be for a simple order item like a lab test where, e.g., the workspace would open to allow the user to enter schedule information (urgency, number of times per day, etc. . . . ) but for a medication order the details would include elements like dose, dose form, special instructions and others. The user can attach a reference to an item in the order set. The reference can either be evidence from an information provider or any other valid internet address. The order set editor also allows the user to attach internal notes and tasks to items in the order set.

In one embodiment, when a user edits an order set it is checked out to that user and cannot be edited by another user until it has been checked back in. This is to ensure that two users do not edit the order set at the same time which would result in content corruption.

When the user is in the order set editor each change is sent back to the server and stored in a binary cache file so that if the internet connection is lost the last changes are preserved and available when the user returns and edits the order set.

Using the content editor, a user can expand and contract the logical structure of the content and see the items with the links to evidence where applicable. For example, the user may open an item to modify it or may choose to add a new item. Structured content can be represented in a number of ways. For example:

A single orderable item like a lab test or medication may be represented by a PIVOT term, A reminder or free text narrative can be inserted in the content to explain something to the user executing the structured content in their workflow, and A protocol which is a pointer to another, separate content structure, can be used to nest structures together where necessary.

In one embodiment, when a user chooses to add or edit an item, the editor opens up a unique interface feature, referred to as a workspace. The workspace graphically expands the area containing the item; this expansion occurs in the display to accommodate the details required to populate all of the data that is unique and required for the type of item that is being modified. This action is referred to as opening a workspace. When the user is done making changes, the workspace is closed and the display reverts to the standard view of the item within the structure (with appropriate modifications to reflect changes made to the data).

Any item in the structure can be linked to evidence provided by an information provider or an external source (e.g., an internet URL) for reference at a later time. For example, if a user needs to link to evidence she can open the evidence browser which allows her to search for the evidence she feels supports the item in question. The user can also attach notes or tasks to an item in the structure. These notes and tasks are for the users of the authoring environment within the authoring environment and are not exported to the target system.

When content is accessed with the content editor, the content is checked out to ensure that multiple authors are not trying to modify the same piece of content simultaneously. If one user attempts to edit a piece of content that has been checked out by another, a message is displayed explaining that the content is already checked out and shows the user name of the user who has it locked. During an edit session, the content editor streams every change made back to the server and those changes are saved to a 'check-out' file. Should the user lose their internet connection, their changes are preserved and will be available the next time they edit that content item. The content remains in a checked out state and can only be edited by the user who was working on it at the time the connection was lost (though administrative overrides or time-outs may be implemented to prevent "permanent" lock-out of an item). When a user is done making changes they can save their changes and check in the content.

Figure 10:
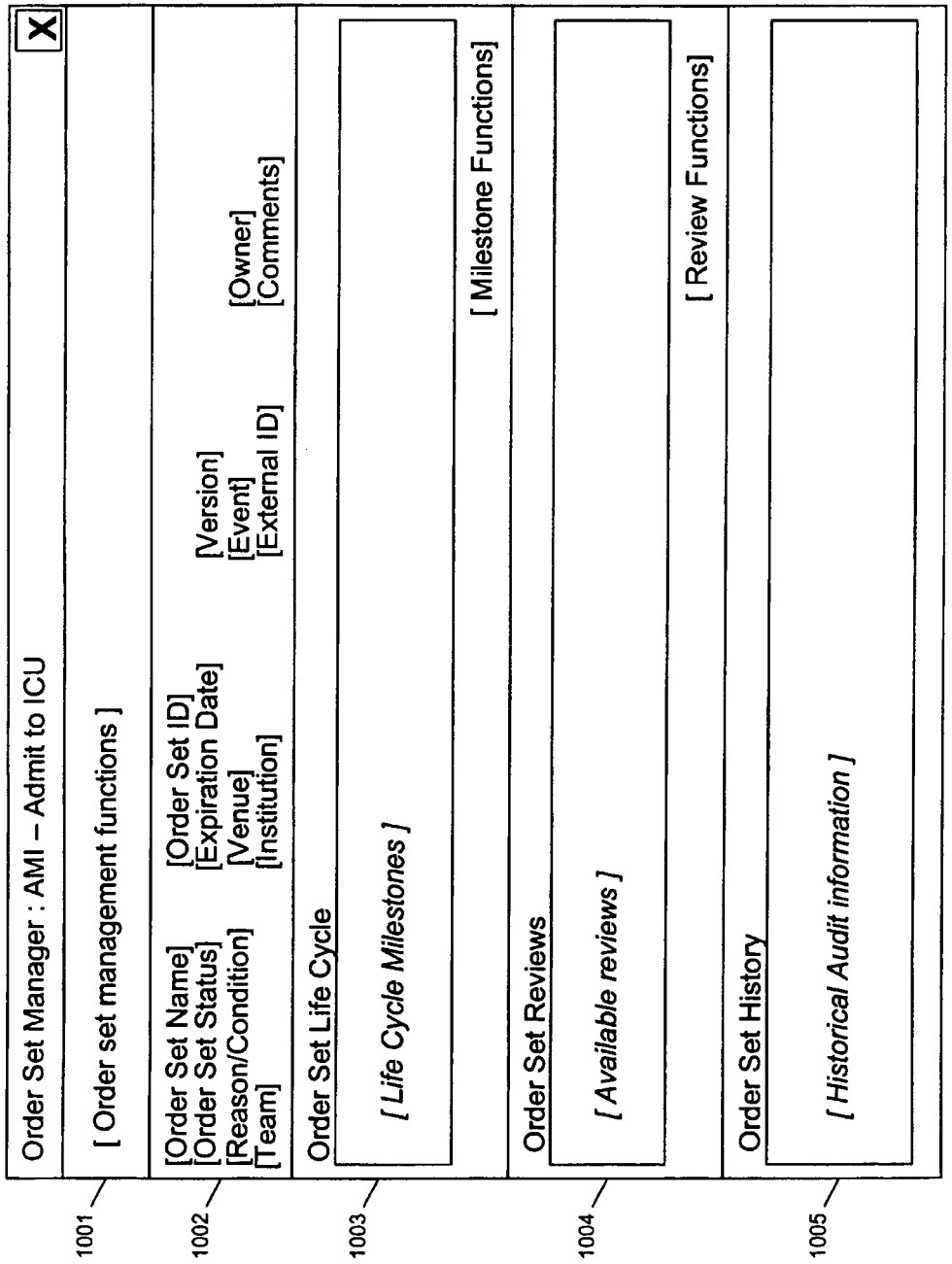
FIG. 10 is an illustrative example of the user interface in a preferred embodiment of the present invention displaying the order set manager.

Referring to FIG. 10, a content manager allows the user to change how the content fits into its environment. For example, changes can be made to:

The meta-data (Reason, Venue, Event, etc) that the content item is linked to,

The team that has rights to modify the content,

When the content expires,

The milestones that have been achieved relative to the content,

The system status of the content in the authoring environment (Draft, Review, Released, Retired), and Whether or not the content item is shown in the public View Space for the environment.

When a content item is created, either from scratch or via the duplication of an existing work, it is stamped with a unique ID and a version number. This version number is fixed when the content is released in the content manager. If a user chooses to edit a released content item a new draft with the same unique ID is created. When the new draft is released the content manager automatically retires the previous version and stamps the newly released content with the next version number. Preferably, retired versions of content are saved and can be viewed as they existed at the time they were retired. If the user sets an expiration date for the content item in the content manager, the Authoring environment notification system will alert the owner of the content when the expiration date arrives.

The content item can be linked to meta-data tags that help the consuming healthcare application determine when to show the content to their user. The meta-data tags relate the content to certain conditions, procedures or symptoms, a venue or location, a patient event and a specific institution if applicable.

The Content Review Tool. The content review tool allows the user to review a content item and make remarks for the author. These reviews are kept with the draft version of the order set.

The Global Content Editor. The global content editor is a tool that allows a user to execute bulk search and replaces across all of the released content in their environment. This can be used where, e.g., a particular item (e.g., a particular drug or treatment) is determined to be hazardous and needs to be removed from all content items as soon as possible. Using the global content editor the user can quickly remove or replace those items and quick release the resulting new versions of those content items.

The Notification Manager. The notification manager is designed to notify the user when something happens that has relevance to them or a content item that they are responsible for. Events that potentially trigger the notification manager include new releases of content items, expiration of content items, and relevant changes to source content or evidence. In one embodiment, the notification manager posts a notice in the user's authoring environment home page and optionally email the notice to the email address listed in the user's profile.

Exporting Content. An embodiment of the authoring environment includes a database to provide awareness of the healthcare applications used by an institution and has the facility to map PIVOT codes to the relevant local or standard vocabularies required by those applications. When a user chooses to export a content item, the user is presented with a choice of predefined exports. In one embodiment, the authoring environment has a standard XML export format as well as the custom formats built for each system vendor.

Related Environments. An embodiment of an authoring environment has the ability to relate environments to one another for the purposes of sharing content. In some cases it could be that the health network has a parent environment and each hospital in the network has a child environment. Each child would be able to see content that was authored at the network level and visa versa. This also facilitates the notion of a content sharing community.

Still referring to FIG. 10, once the user has modified the order set in the order set editor, the user can then manage the definitive characteristics, the condition, the venue and event the order set is mapped to as well as change the status of the order set using the order set manager.

For example, on the order set manager page the user has functions they can perform relative to the order set 1001. These functions can very depending on the status of the order set. The characteristics of the order set 1002 are the things that define the order set. The user can add and update environment specific lifecycle events to the order set 1003. The user can post a review of the order set from this page, or from the viewspace portal. In either case the reviews can be viewed from the page as well 1004. All changes made to the order set are logged in the audit trail database. Major changes may be displayed in the order set history list box on this page 1005. From this page the user can also mark the order set as a protocol, which allows it to be virtually linked into other order sets, or publish the order set into the environment's viewspace, which allows users who do not have access to the authoring environment to see the content on, for example, a reference website.

Figure 11:
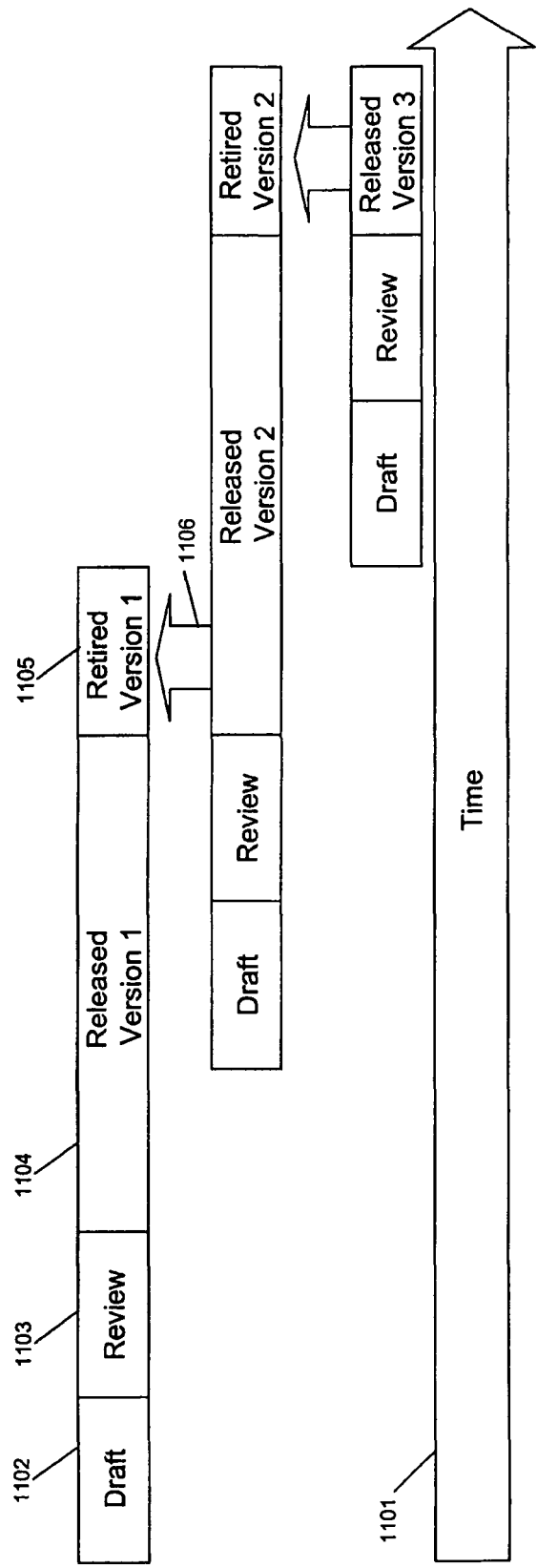
FIG. 11 is a schematic illustration of how the status of content in an authoring environment changes throughout its lifecycle in the system of the present invention.

Referring to FIG. 11, in one embodiment, changing the status of an order set, for example using the order set manager of FIG. 10, has ramifications with respect to the life cycle of an order set. These statuses are schematically depicted in the figure. When an order set is initially duplicated from the default order set, or created as blank, the order set is assigned an ID and has a status of draft 1102. While in draft status, the order set can be edited. Upon initial completion, the status of the order set can be changed to review 1103, which disables editing and allows users to post reviews of the order set. The user can then change the status back to draft 1102 to make additional edits in response to the reviews, or update the status to released 1104. When the order set is released, it is stamped with a version number and permanently locked. If the user should decide to edit the order set a new draft is created. When the new draft is ultimately released 1106 it is stamped with the next version number and the previously released version is automatically retired 1105. Preferably, retired versions of order sets are permanently stored for reference purposes. A user can abort a new draft without impacting a previously released version of the order set.

Figure 12:
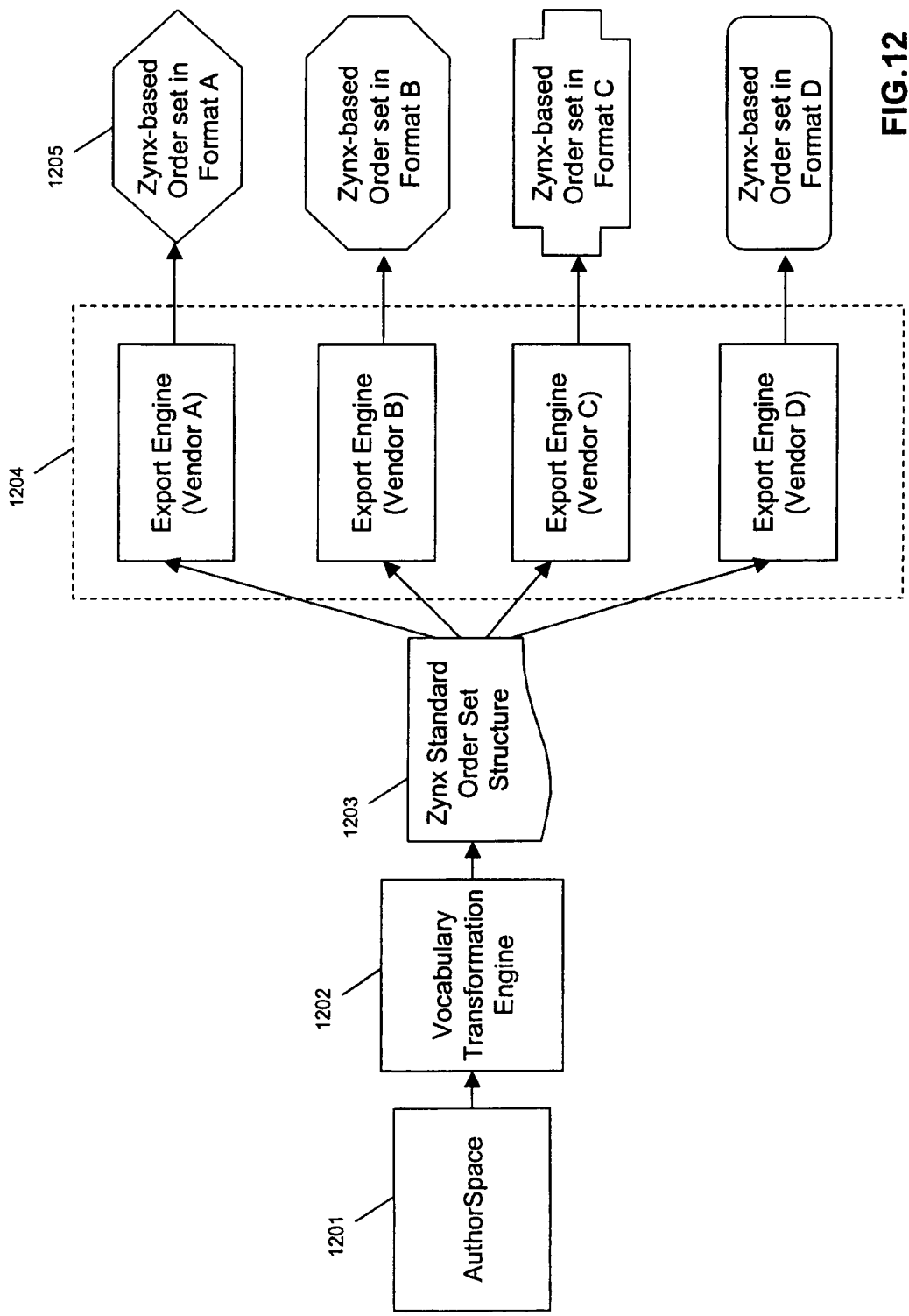
FIG. 12 is a schematic illustration of the export process in the system of the present invention.

Referring to FIG. 12, once a user is done editing the order set and has released it, they export the order set. An exemplary embodiment of an export process is depicted in FIG. 12. In order to resolve the issue of portability of content, embodiments of the present invention have the ability to transform both the terms used in the definition of the order set and the structural format of the order set in order to make it consumable within any healthcare application. When the order set is exported from the authoring environment 1201, the terminology is transformed 1202 by the vocabulary mapping functionality, as depicted with reference to FIG. 4, and the resulting order set is created in a standard structure 1203. This structure may then be converted by a custom export engine 1204. The result is an export structure 1205 that is in the format required by the vendor system using the terms from the users local catalog.

It is noteworthy that depending on the healthcare application, the target vocabulary of the final version of the file could be a standard vocabulary 403, a vendor vocabulary that spans vendor customers 404, or a local catalog just for the hospital in question 405. The vocabulary mapping functionality 402 allows for the mapping of any of these to the standard term vocabulary 401.

Figure 13:
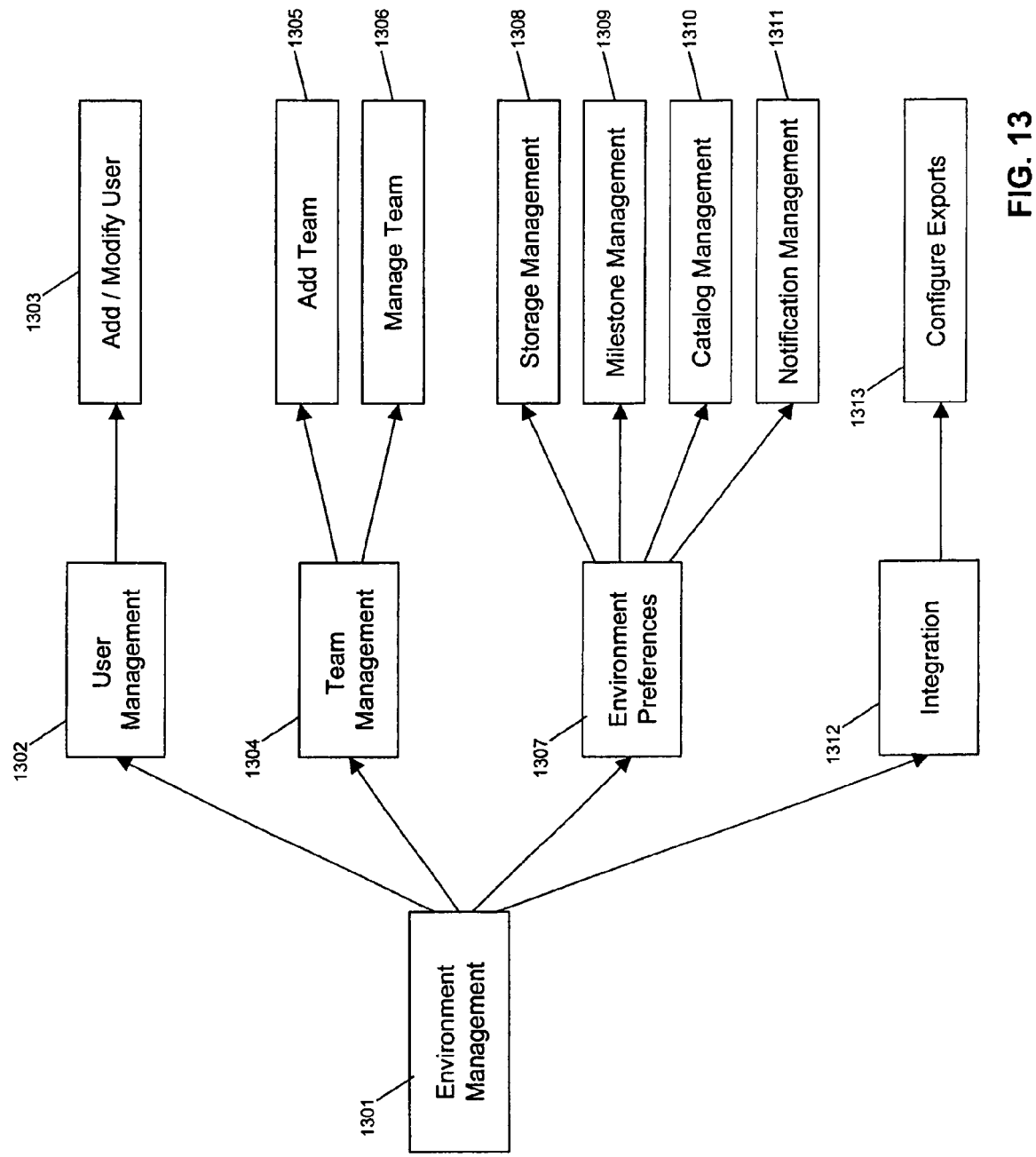
FIG. 13 is a schematic illustration of the environment management functions in the system of the present invention.

Referring to FIG. 13, one or many users in a given environment may be assigned the privileges of the environment manager. This privilege allows the user to access the environment manager link on the main page in the activities section 703 (FIG. 7). The environment management functions are depicted in FIG. 13. Once on the environment management page 1301, the user can perform several functions relating to the management of their environment. These include user management 1302, team management 1304, environment preferences 1307 and integration options 1312.

User management 1302 allows the environment manager to add or modify users that have access to the environment 1303. By adding the user to the environment, for example, they may give them view access on the base team in the authoring environment.

Team Management 1304 allows the environment manager to create 1305 and manage 1306 teams. Managing the team is where users with access to the environment are added to teams and given team specific privileges that relate to the content that is owned by the team in question.

Environment Preferences 1307 is where many of the configurable options for the environment can be manipulated by the environment manager. Storage management 1308 allows the environment manager to create and organize their folder structure for storing their localized content. Milestone management 1309 allows the environment manager to create content life cycle milestones that will be used in the order set manager to measure local progress on order set development. Catalog management 1310 allows the environment manager to add terms to authoring environment that are not in the standard catalog. These new terms can be accessed by any environment user while in the order set editor. Notification management 1311 allows the environment manager to attach milestone notifications to users in the environment.

Integration 1312 is where the environment manager can create allowable exports that can be selected by the environments users when they choose to export an order set. Each environment is associated with one or many healthcare application vendors by administrative client services personnel depending on what systems they have in their health network or hospital. These exports can be configured by associating export vocabularies with a given export so that the proper terms are populating the right format.

Figure 14:
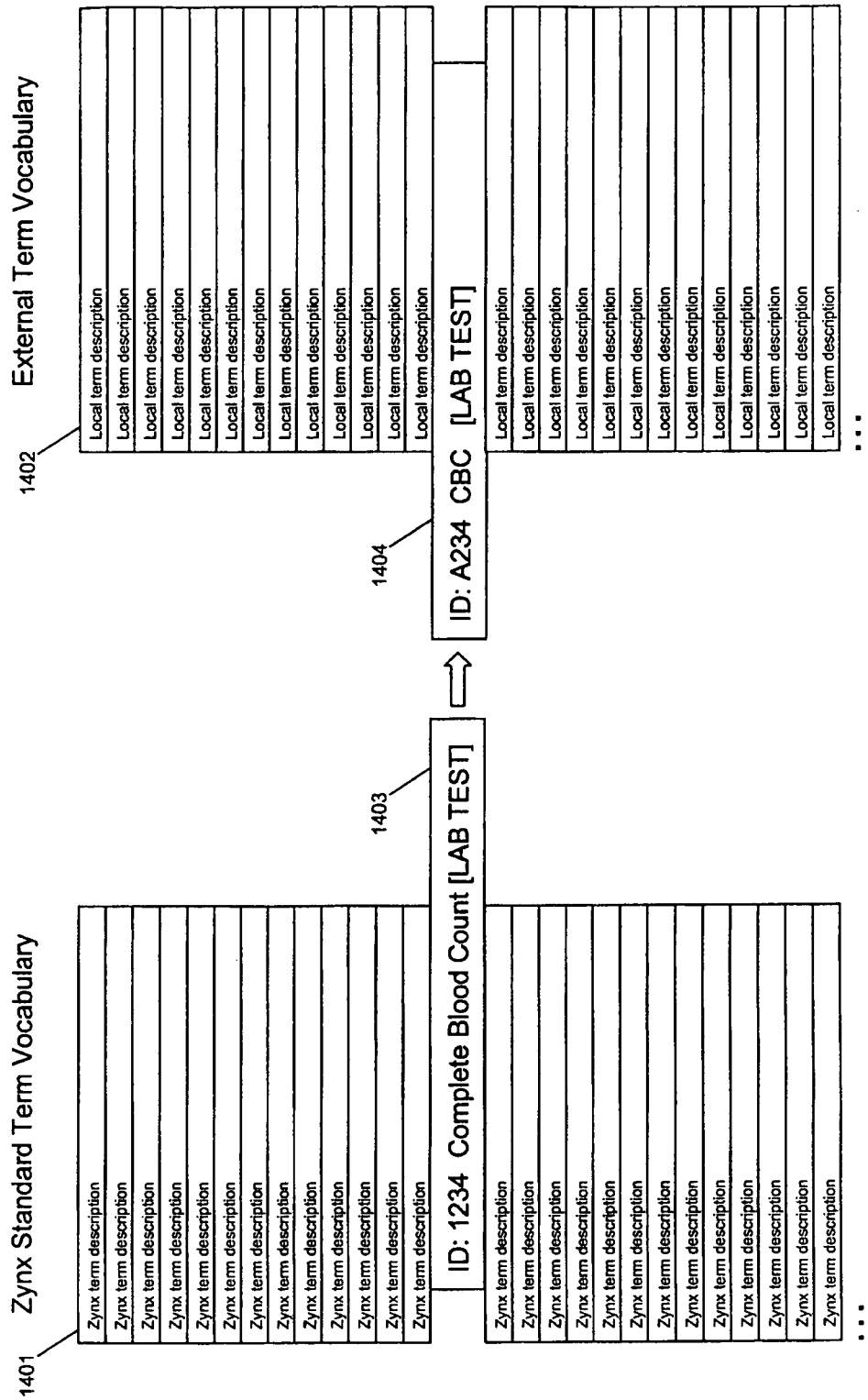
FIG. 14 is a schematic illustration of the concept of terminology mapping in the system of the present invention.

Vocabulary management functionality in the present invention is used to support the transformation of the localized content into a form that is consumable by the end user's healthcare application. Term mapping is the relating of identical terms in two distinct vocabularies FIG. 14 illustrates an example of the concept of term mapping. In this case the standard term vocabulary 1401 has a term representing a 'Complete Blood Count' lab test 1403. The external vocabulary 1402 has a term 'CBC' 1404 that has the exact same meaning as the previously mentioned term in the standard term vocabulary. These two terms could then be mapped so that every time the user selects the 'Complete Blood Count' term in the authoring environment that item can be expressed to the consuming application with the 'CBC' identifier so that it can be understood.

Figure 15:
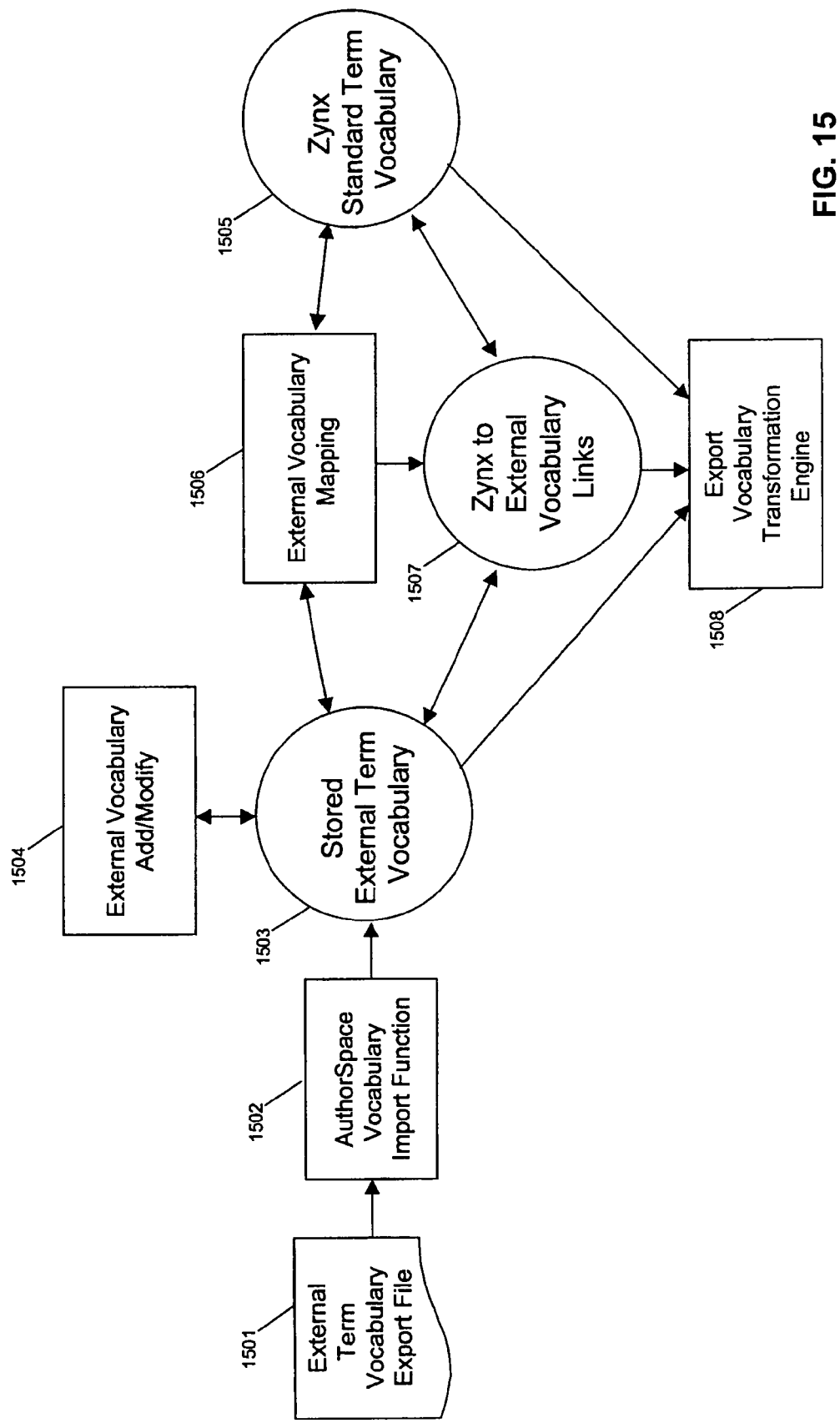
FIG. 15 is the schematic representation of the external vocabulary import and mapping process in the system of the present invention.

Referring to FIG. 15, an embodiment of a process used to import and map external vocabularies is depicted. The user may export a file from their healthcare application containing the terms from their orders catalog 1501. The authoring environment's vocabulary import function 1502 processes the file based upon parameters provided by the user and stores the external terms in a database 1503 relative to the user's environment. At this point, the user may add or modify terms using the vocabulary maintenance functions 1504. The bulk of the effort would be in the mapping of the external terms to the standard term vocabulary 1505. Using the authoring environment vocabulary mapping tool 1506, the user would establish links 1507 between the stored external terms 1503 and the standard vocabulary terms 1505. These links will later be used by the export vocabulary transformation engine 1508 to transform the standard terms in the order set structures into the term that can be understood by the user's healthcare application.

The invention may be implemented in digital electronic circuitry, or in computer hardware, firmware, software, or in combinations of them. Apparatus of the invention may be implemented in a computer program product tangibly embodied in a machine-readable storage device for execution by a programmable processor; and method steps of the invention may be performed by a programmable processor executing a program of instructions to perform functions of the invention by operating on input data and generating output. The invention may advantageously be implemented in one or more computer programs that are executable on a programmable system including at least one programmable processor coupled to receive data and instructions from, and to transmit data and instructions to, a data storage system, at least one input device, and at least one output device. Each computer program may be implemented in a high-level procedural or object-oriented programming language, or in assembly or machine language if desired; and in any case, the language may be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing may be supplemented by, or incorporated in, specially-designed ASICs (application-specific integrated circuits).

A number of embodiments of the present invention have been described. Nevertheless, it will be understood that various modifications may be made without departing from the spirit and scope of the invention.

What is claimed is:

1. A system for collaborative review of a clinical content structure, the system comprising:
    a server configured to display a first default clinical content structure provided by an information provider to a first set of users of a first authoring environment for reviewing and modifying the first default clinical content structure, wherein the clinical content structure comprises a set of one or more evidence-based options that are selectable by a clinician during patient care and the first authoring environment operates on a first set of one or more programmed computers associated with a first protocol;
    a server configured to display the first default clinical content structure to a second set of users of a second authoring environment for reviewing and modifying the first default clinical content structure, wherein the second authoring environment operates on a second set of one or more programmed computers associated with a second protocol, the first set of one or more programmed computers and the second set of one or more programmed computers are communicatively coupled to a server via a network, and the first protocol and the second protocol are different;
    a server configured to enable the first set of users and the second set of users to collaboratively input modification data associated with the first default clinical content structure by granting the first set of users access to the first authoring environment and granting the second set of users access to the second authoring environment;
    a server configured to modify the first default clinical content structure based on the modification data received from the first set of users of the first authoring environment and the second set of users of the second authoring environment to create a modified clinical content structure;
    a server configured to store a first plurality of data translation rules associated with the first authoring environment, wherein each data translation rule of the first plurality of data translation rules maps at least one term associated with the first authoring environment to one or more terms of one or more standard term libraries;
    a server configured to store a second plurality of data translation rules associated with the second authoring environment, wherein each data translation rule of the second plurality of data translation rules maps at least one term associated with the second authoring environment to one or more terms of the one or more standard term libraries;
    a server configured to automatically translate the modified clinical content structure into a first standard structure using the first plurality of data translation rules;
    a server configured to automatically translate the modified clinical content structure into a second standard structure using the second plurality of data translation rules;
    a server configured to convert the first standard structure into a first export structure that is executable by the first protocol of the first set of one or more programmed computers;
    a server configured to convert the second standard structure into a second export structure that is executable by the second protocol of the second set of one or more programmed computers;
    a server configured to transmit the first export structure to the first set of one or more programmed computers and the second export structure to the second set of one or more programmed computers;
    a server configured to identify a second default clinical content structure that comprises an updated version of the first default clinical content structure; and
    a server configured to provide the second default clinical content structure to the first set of users of the first authoring environment and the second set of users of the second authoring environment, wherein the first set of users and the second set of users are enabled to use the second default clinical content structure.

2. The system of claim 1 wherein, if the first authoring environment and the second authoring environment are related through a common network, a user in the first authoring environment may be granted limited access to the second authoring environment.

3. The system of claim 2 wherein a user in the second authoring environment may be granted limited access to the first authoring environment.

4. The system of claim 2 wherein the common network is a common health network.

5. The system of claim 1 wherein the clinical content structure comprises an order set.

6. The system of claim 1 wherein the system is a web-based system.

7. The system of claim 1 wherein the authoring environments are associated with different medical institutions.

8. The system of claim 1 wherein a user's access to an authoring environment is controlled by a password.

9. The system of claim 1 wherein a user's access to an authoring environment is view-only.

10. The system of claim 1 wherein access to an authoring environment is granted to a user based on their role on a team.

11. The system of claim 1 wherein a user's access includes content rights.

12. A method for collaborative review of a clinical content structure operating on a programmed computer, the method comprising:
displaying, using a server, a first default clinical content structure provided by an information provider to a first set of users of a first authoring environment for reviewing and modifying the first default clinical content structure, wherein the clinical content structure comprises a set of one or more evidence-based options that are selectable by a clinician during patient care and the first authoring environment operates on a first set of one or more programmed computers associated with a first protocol;
displaying, using a server, the first default clinical content structure provided by an information provider to a second set of users of a second authoring environment for reviewing and modifying the first default clinical content structure, wherein the second authoring environment operates on a second set of one or more programmed computers associated with a second protocol, the first set of one or more programmed computers and the second set of one or more programmed computers are communicatively coupled to a server via a network, and the first protocol and the second protocol are different;
enabling, using a server, the first set of users and the second set of users to collaboratively input modification data associated with the first default clinical content structure by granting the first set of users access to the first authoring environment and granting the second set of users access to the second authoring environment;
modifying, using a server, the first default clinical content structure based on the modification data received from the first set of users of the first authoring environment and the second set of users of the second authoring environment to create a modified clinical content structure;
storing, using a server, a first plurality of data translation rules associated with the first authoring environment, wherein each data translation rule of the first plurality of data translation rules maps at least one term associated with the first authoring environment to one or more terms of one or more standard term libraries;
storing, using a server, a second plurality of data translation rules associated with the second authoring environment, wherein each data translation rule of the second plurality of data translation rules maps at least one term associated with the second authoring environment to one or more terms of the one or more standard term libraries;
automatically translating, using a server, the modified clinical content structure into a first standard structure using the first plurality of data translation rules;
automatically translating, using a server, the modified clinical content structure into a second standard structure using the second plurality of data translation rules;
converting, using a server, the first standard structure into a first export structure that is executable by the first protocol of the first set of one or more programmed computers;
converting, using a server, the second standard structure into a second export structure that is executable by the second protocol of the second set of one or more programmed computers;
transmitting, using a server, the first export structure to the first set of one or more programmed computers and the second export structure to the second set of one or more programmed computers;
identifying, using a server, a second default clinical content structure that comprises an updated version of the first default clinical content structure; and
providing, using a server, the second default clinical content structure to the first set of users of the first authoring environment and the second set of users of the second authoring environment, wherein the first set of users and the second set of users are enabled to use the second default clinical content structure.

13. The method of claim 12 wherein, if the first authoring environment and the second authoring environment are related through a common network, a user in the first authoring environment may be granted limited access to the second authoring environment.

14. The method of claim 13 wherein a user in the second authoring environment may be granted limited access to the first authoring environment.

15. The method of claim 13 wherein the common network is a common health network.

16. The method of claim 12 wherein the clinical content structure comprises an order set.

17. The method of claim 12 wherein the system is a web-based system.

18. The method of claim 12 wherein the authoring environments are associated with different medical institutions.

19. The method of claim 12 wherein a user's access to an authoring environment is controlled by a password.

20. The method of claim 12 wherein a user's access to an authoring environment is view-only.

21. The method of claim 12 wherein access to an authoring environment is granted to a user based on their role on a team.

22. The method of claim 12 wherein a user's access includes content rights.

23. A method of processing and distributing clinical content structures, the method comprising:
providing by at least one computer system a clinical content structure template, comprising an order set template, that utilizes a first format;
enabling at least a first user, via an authoring environment associated with a first protocol, and
a second user, via an authoring environment associated with a second protocol,
to collaboratively input modification data associated with the clinical content structure;
modifying the clinical content structure template, based at least in part on the modification data, to create a modified clinical content structure;
accessing, by at least one computer system, a first plurality of data translation rules,
wherein the first plurality of data translation rules includes at least one rule that maps at least one term associated with the modified clinical content structure to a corresponding first localized term;

translating, by at least one computer system, the modified clinical content structure using the first plurality of data translation rules to provide a first customized order set in a first localized format;

providing, by at least one computer system, at least one user access to the first customized order set in the first localized format;

accessing, by at least one computer system, a second plurality of data translation rules,
wherein the second plurality of data translation rules includes at least one rule that maps at least one term associated with the modified clinical content structure to a corresponding second localized term;

translating, by at least one computer system, the modified clinical content structure using the second plurality of data translation rules to provide a second customized order set in a second localized format; and providing, by at least one computer system, at least one user access to the second customized order set in the second localized format.

24. The method as defined in claim 23, the method further comprising:
receiving an indication that a new version of the first customized order set has been generated; and
transmitting a notification regarding the new version to one more users that utilized the first customized order set prior to the generation of the new version of the first customized order set.

25. The method as defined in claim 23, wherein the first customized order set is generated from a copy of the clinical content structure template.

26. The method as defined in claim 23, wherein the first customized order set has a different structure than the clinical content structure template.

27. A computer system programmed to process clinical content structures, comprising:
at least one computing device;
non-transitory computer-readable media storing instructions that when executed by the at least one computing device are configured to cause the computer system to perform operations comprising:
providing a clinical content structure template that utilizes a first format;
enabling at least a first user, via an authoring environment associated with a first protocol, and
a second user, via an authoring environment associated with a second protocol,
to collaboratively input modification data associated with the clinical content structure;
modifying the clinical content structure template, based at least in part on the modification data, to create a modified clinical content structure;
accessing a first plurality of data translation rules,
wherein the first plurality of data translation rules includes at least one rule that maps at least one term associated with the modified clinical content structure to a corresponding first localized term;
translating the modified clinical content structure using the first plurality of data translation rules to provide a first customized order set in a first localized format;
providing at least one user access to the first customized order set in the first localized format;
accessing a second plurality of data translation rules,
wherein the second plurality of data translation rules includes at least one rule that maps at least one term associated with the modified clinical content structure to a corresponding second localized term;
translating the modified clinical content structure using the second plurality of data translation rules to provide a second customized order set in a second localized format; and
providing at least one user access to the second customized order set in the second localized format.

28. The system as defined in claim 27, the operations further comprising:
receiving an indication that a new version of the first customized order set has been generated; and
transmitting a notification regarding the new version to one more users that utilized the first customized order set prior to the generation of the new version of the first customized order set.

29. The system as defined in claim 27, wherein the first customized order set is generated from a copy of the clinical content structure template.

30. The system as defined in claim 27, wherein the first customized order set has a different structure than the clinical content structure template.

* * * * *